(12) United States Patent
Hansen et al.

(10) Patent No.: US 7,033,172 B2
(45) Date of Patent: Apr. 25, 2006

(54) DENTAL POSITIONING GRID

(75) Inventors: Steven J. Hansen, Penfield, NY (US); Thomas P. Rock, Rochester, NY (US)

(73) Assignee: Eastman Kodak Company, Rochester, NY (US)

( * ) Notice: Subject to any disclaimer, the term of this patent is extended or adjusted under 35 U.S.C. 154(b) by 299 days.

(21) Appl. No.: 10/417,069

(22) Filed: Apr. 16, 2003

(65) Prior Publication Data

US 2004/0209221 A1 Oct. 21, 2004

(51) Int. Cl.
*A61C 1/00* (2006.01)
*A61B 1/04* (2006.01)

(52) U.S. Cl. .................. 433/29; 433/215; 433/229; 396/16

(58) Field of Classification Search ............ 433/29, 433/215, 229; 396/16
See application file for complete search history.

(56) References Cited

U.S. PATENT DOCUMENTS

| | | | | |
|---|---|---|---|---|
| 3,685,053 A | * | 8/1972 | Kirkpatrick | 342/401 |
| 4,216,589 A | * | 8/1980 | Beaver | 33/266 |
| 6,094,545 A | * | 7/2000 | Petitjean | 396/544 |
| 6,181,377 B1 | * | 1/2001 | Kobayashi | 348/333.02 |
| 6,431,768 B1 | * | 8/2002 | Nakamura | 396/348 |
| 6,468,676 B1 | * | 10/2002 | Ueda et al. | 428/690 |

* cited by examiner

*Primary Examiner*—John J Wilson
(74) *Attorney, Agent, or Firm*—William F. Noval

(57) ABSTRACT

In a digital camera having a rectangular electronic display for framing pictures, a dental positioning grid comprising: a line pattern superimposed on the rectangular electronic display, the line pattern including a horizontally centered horizontal line extending substantially the width of the display, a short vertical line intersecting the horizontal line at its midpoint, and long left and right vertical lines intersecting the horizontal line at substantially ¼ of the display width distance respectively from the left and right sides of the display.

2 Claims, 3 Drawing Sheets

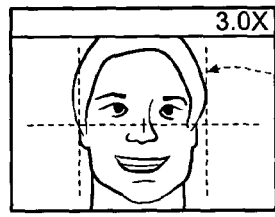
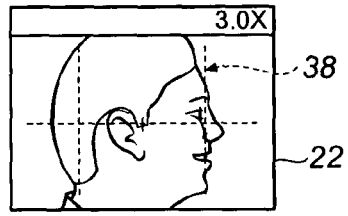
FIG. 6A　　　　FIG. 6B
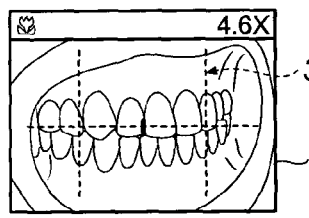
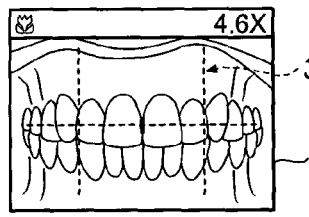
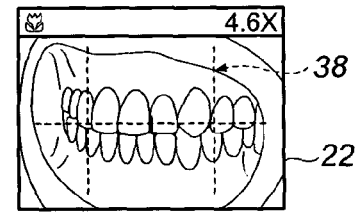
FIG. 7A　　　FIG. 7B　　　FIG. 7C
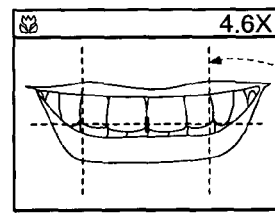
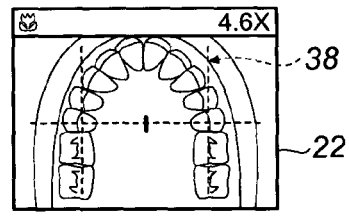
FIG. 7D　　　　FIG. 7E
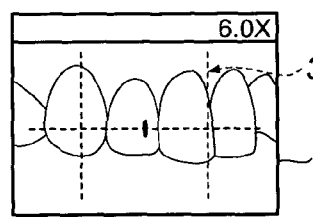
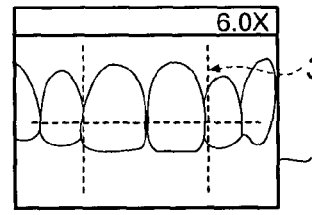
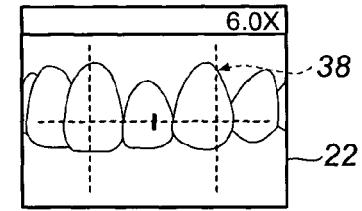
FIG. 8A　　　FIG. 8B　　　FIG. 8C

DENTAL POSITIONING GRID

FIELD OF THE INVENTION

This invention relates in general to dental photography using a digital camera that has an on board electronic preview screen, and more particularly to a dental positioning grid superimposed on the screen and designed to facilitate framing of the photograph.

BACKGROUND OF THE INVENTION

The American Academy of Cosmetic Dentistry (AACD) publishes *A Guide to Accreditation Photography* that describes the requirements and techniques for photographic documentation and evaluation in cosmetic dentistry. The guide contains specific requirements for proper framing of many types of dental photographs. Generic reticles found in conventional camera viewfinders and optical devices are not designed for a specific dental application. Moreover, use of conventional film cameras is time consuming since the film must be developed before it can be shown to a patient. The introduction of digital cameras has obviated the shortcomings of film based cameras but the framing reticles are still not directed to specific dental applications. There is thus a need for improvement in dental photography.

SUMMARY OF THE INVENTION

According to the present invention, there is provided a fulfillment of this need.

According to a feature of the present invention, there is provided in a digital camera having a rectangular electronic display for framing pictures, a dental positioning grid comprising:

a line pattern superimposed on said rectangular electronic display, said line pattern including a horizontally centered horizontal line extending substantially the width of said display, a short vertical line intersecting said horizontal line at its midpoint, and long left and right vertical lines intersecting said horizontal line at substantially ¼ of the display width distance respectively from the left and right sides of said display.

ADVANTAGEOUS EFFECT OF THE INVENTION

The invention has the following advantages.

1. Using the invention to frame the subject as shown will establish the proper camera-to-subject distance.
2. Helps keep horizontal orientation with the occlusal plane.
3. Center crosshair helps position the area of interest in the center of the lens, which is the region of best focus.
4. Using the vertical lines to position lateral shots gives proper framing according to the AACD guidelines.
5. Helps promote consistent and repeatable results.

BRIEF DESCRIPTION OF THE DRAWINGS

FIGS. 6A and 6B are diagrammatic views depicting framing of frontal and side views respectively of the full face.

FIGS. 7A, 7B, 7C, 7D and 7E are diagrammatic views depicting framing of various views of full dental sets.

FIGS. 8A, 8B, and 8C are diagrammatic views depicting framing respectively of close-up views of right lateral frontal and left lateral upper dental groups.

DETAILED DESCRIPTION OF THE INVENTION

Figure 1:
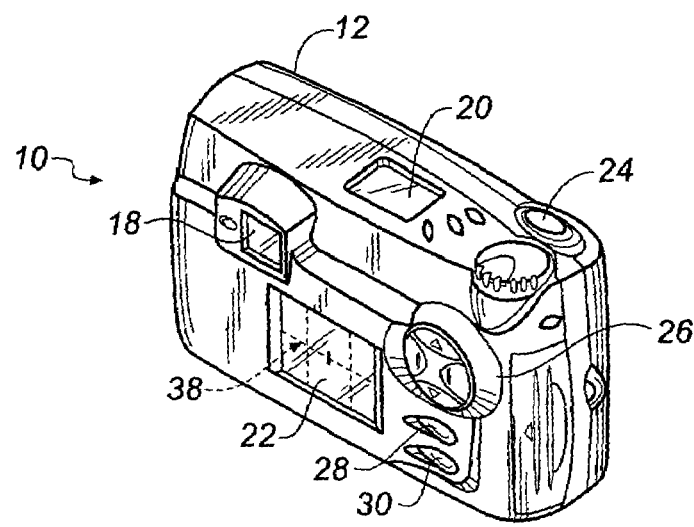
FIG. 1 is a rear perspective view of a digital camera incorporating the present invention.
Figure 2:
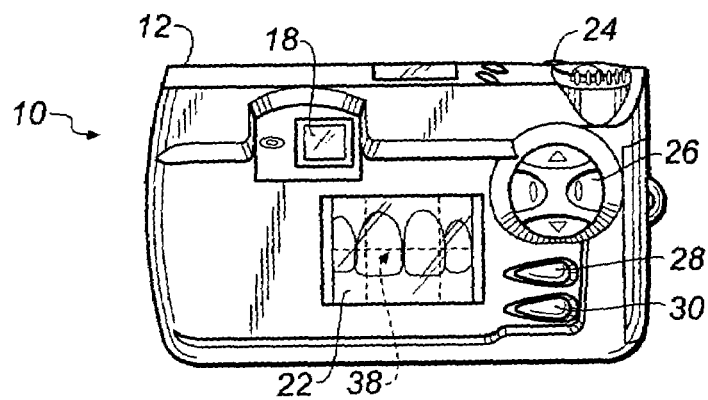
FIG. 2 is a rear elevational view of the digital camera of FIG. 1
Figure 3:
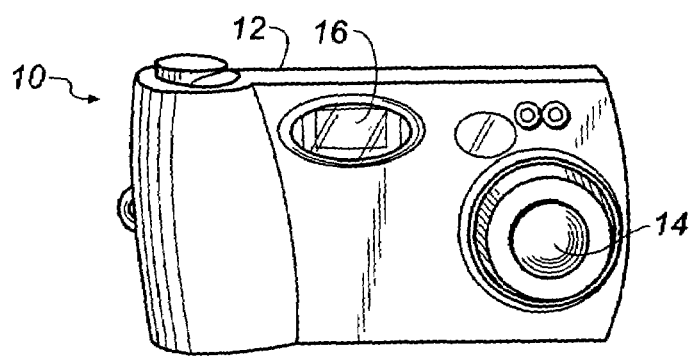
FIG. 3 is a front elevational view of the digital camera of FIG. 1.
Figure 4:
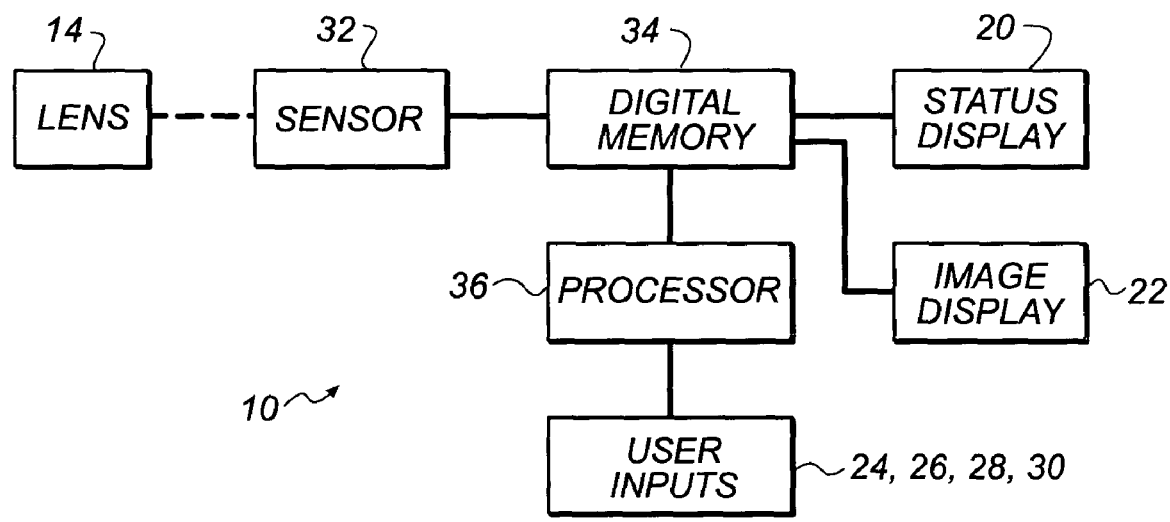
FIG. 4 is a block diagram of the principle components of the digital camera of FIG. 1.

Referring now to FIGS. 1–4 there will be described a digital camera incorporating the dental positioning grid of the present invention. The reticule lines of the grid match up with identifiable anatomy of the face and mouth in a way that facilitates proper distance, angles and framing for dental photography.

As shown, digital camera 10 includes a case 12, lens 14, flash 16, optical view finder 18, status electronic display 20, image (preview) electronic display 22, user input buttons 24, 26, 28, 30, sensor 32, digital memory 34, digital processor 36 and dental positioning grid 38. In operation, a dental object to be photographed is framed by using dental positioning grid 38 superimposed on image electronic display 22. A digital picture is taken by actuating shutter button 24, which exposes sensor 32 to the dental object through lens 14. The dental photograph is temporarily stored in digital memory 34 and then stored on a removable memory (not shown) or transmitted by wired or wireless transmission channel to a computer or network. Digital processor 36 controls the components of digital camera 10 under the control of user inputs 24–30.

Figure 5:
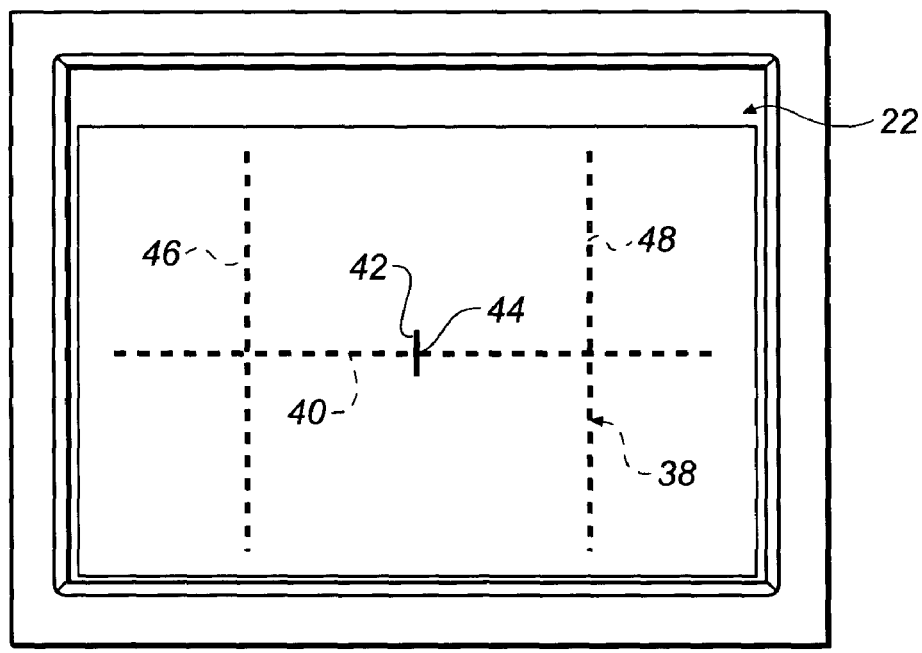
FIG. 5 is a diagrammatic view of the dental positioning grid of the present invention superimposed on an electronic display.

According to the present invention; dental positioning grid 38 superimposed on image electronic display 22 is used to frame dental objects. As shown in FIG. 5, grid 38 constitutes a line pattern which includes a horizontally centered horizontal line 40 extending substantially the width of display 22, a short vertical line 42 intersecting horizontal line 40 at its midpoint 44 and left and right long vertical lines 46 and 48 intersecting horizontal line 40 at substantially ¼ of the width of display 22 respectively from left and right sides of display 22. Grid 38 can be permanently printed on display 22 (e.g., by screen printing), can be formed on a transparent support which overlays display 22, or can be electronically displayed as a graphic overlay on the electronic display 22.

The most common dental photographs are taken at what have conventionally been called magnification ratios of "1:10", "1:2", and "1.1". The lines of grid 38 match up with identifiable anatomy of the face and mouth in a way that facilitates proper distance, angles, and framing for dental photography. The proper positioning of the lines of grid 38 relative to the subject for these common dental photographs are shown in the following Figures.

Referring now to FIGS. 6A and 6B, photographing the full face (1:10) is shown respectively in frontal and side views of a subject. In FIG. 6A, the full frontal face is framed by locating the sides of the face touching the left and right vertical lines 46 and 48 and the nose at short vertical line 42 at the center of line 40. The side of the face and head is framed in FIG. 6B by locating the front and rear of the head substantially between vertical lines 46 and 48 and by locating the central vertical line 42 just in front of the ear.

FIGS. 7A, 7B and 7C show framing fill mouth views (1:2) of complete dental set of upper and lower teeth with grid 38. FIG. 7A shows a right lateral view, FIG. 7B shows a frontal view and FIG. 7C shoes a left lateral view. In FIG. 7B, the central vertical line 42 located at the center of the dental set and the horizontal line 40 is located aligned with a line between the upper and lower sets of teeth. In FIGS. 7A and 7C, the outer end of the teeth sets as located at the right or left vertical lines respectively. FIG. 7D shows framing of a frontal view of the upper dental set and FIG. 7E shows framing of the full arch of a dental set.

FIGS. 8A, 8B and 8C show framing of close-up dental photographs (1:1) of respectively a right lateral view, a frontal view and a left lateral view. As shown in FIG. 8B, the short vertical center line is located between the two front teeth and the left and right vertical lines are located substantially at the left and right sides of the two front teeth.

The invention has been described in detail with particular reference to certain preferred embodiments thereof, but it will be understood that variations and modifications can be effected within the spirit and scope of the invention.

PARTS LIST 10 digital camera
12 case
14 lens
16 flash
18 optical view finder
20 status electronic display
22 image (preview) electronic display
24–30 user input buttons
32 sensor
34 digital memory
36 digital processor
38 dental positioning grid
40 centered horizontal line
42 short vertical line
44 midpoint
46,48 long vertical lines

What is claimed is:

1. A method of taking full frontal face and side head and face dental photographs comprising:
    providing a digital camera having a rectangular electronic display;
    providing a line pattern superimposed on said display, said line pattern including a horizontally centered horizontal line extending substantially the width of said display, a short vertical line intersecting said horizontal line at its midpoint and left and right long vertical lines intersecting said horizontal line at substantially ¼ of the display width distance respectively from the left and right sides of said display;
    framing the full frontal dental set of an individual by locating the sides of the face at said left and right vertical lines and the nose at said short vertical line at the center of said horizontal line and taking a photograph;
    framing the dental set at the side of the face and head of an individual by locating the front and rear of said head at said left and right vertical lines, and by locating just in front of said ear at said short vertical line and taking a photograph; and
    wherein proper distance, angles, and framing for said dental photographs of the individual at a magnification ratio of "1:10" is facilitated
    wherein the full frontal dental set of a closed mouth is photographed after it is framed by locating the short vertical line at the center of the dental set and aligning said horizontal line with the line between the upper and lower sets of teeth and wherein the left and right lateral view of the full set of teeth is framed by aligning said horizontal line with a line between the upper and lower sets of teeth and locating one of said left or right vertical lines at the outer end of said upper and lower sets of teeth; wherein proper distance, angles, and framing for said dental photographs of the individual at a magnification ratio of "1:2" is facilitated.

2. A method of taking full frontal face and side head and face dental photographs comprising:
    providing a digital camera having a rectangular electronic display
    providing a line pattern superimposed on said display, said line pattern including a horizontally centered horizontal line extending substantially the width of said display, a short vertical line intersecting said horizontal line at its midpoint and left and right long vertical lines intersecting said horizontal line at substantially ¼ of the display width distance respectively from the left and right sides of said display;
    framing the full frontal dental set of an individual by locating the sides of the face at said left and right vertical lines and the nose at said short vertical line at the center of said horizontal line and taking a photograph;
    framing the dental set at the side of the face and head of an individual by locating the front and rear of said head at said left and right vertical lines, and by locating just in front of said ear at said short vertical line and taking a photograph; and
    wherein proper distance, angles, and framing for said dental photographs of the individual at a magnification ratio of "1:10" is facilitated
    wherein a close-up of the frontal view of the upper and lower set of teeth of an individual is photographed after it is framed by locating said short vertical line between the two front teeth and by locating said left and right vertical lines substantially at the left and right sides of said two front teeth; wherein proper distance, angles, and framing for said dental photograph of the individual at a magnification ratio of "1:1" is facilitated.

* * * * *